United States Patent
Timmins et al.

(10) Patent No.: US 10,000,787 B2
(45) Date of Patent: Jun. 19, 2018

(54) METHODS FOR DIAGNOSING BACTERIAL INFECTIONS

(71) Applicants: STC.UNM, Albuquerque, NM (US); LOS ALAMOS NATIONAL SECURITY, LLC, Los Alamos, NM (US)

(72) Inventors: Graham Timmins, Albuquerque, MN (US); Louis Pete Silks, Los Alamos, NM (US)

(73) Assignees: STC.UNM, Albuquerque, NM (US); LOS ALAMOS NATIONAL SECURITY, LLC., Los Alamos, NM (US)

( * ) Notice: Subject to any disclaimer, the term of this patent is extended or adjusted under 35 U.S.C. 154(b) by 105 days.

(21) Appl. No.: 14/434,509

(22) PCT Filed: Oct. 8, 2013

(86) PCT No.: PCT/US2013/063827
§ 371 (c)(1),
(2) Date: Apr. 9, 2015

(87) PCT Pub. No.: WO2014/058848
PCT Pub. Date: Apr. 17, 2014

(65) Prior Publication Data
US 2015/0275265 A1 Oct. 1, 2015

Related U.S. Application Data

(60) Provisional application No. 61/711,978, filed on Oct. 10, 2012.

(51) Int. Cl.
| | |
|---|---|
| *C12Q 1/04* | (2006.01) |
| *C12Q 1/02* | (2006.01) |
| *A61B 5/083* | (2006.01) |
| *G01N 33/497* | (2006.01) |
| *G01N 33/569* | (2006.01) |
| *G01N 33/60* | (2006.01) |
| *G21H 5/02* | (2006.01) |
| *A61B 5/08* | (2006.01) |
| *A61B 5/145* | (2006.01) |
| *A61B 5/20* | (2006.01) |

(52) U.S. Cl.
CPC ............. *C12Q 1/04* (2013.01); *A61B 5/0836* (2013.01); *C12Q 1/02* (2013.01); *G01N 33/497* (2013.01); *G01N 33/56911* (2013.01); *G01N 33/60* (2013.01); *A61B 5/082* (2013.01); *A61B 5/14507* (2013.01); *A61B 5/14546* (2013.01); *A61B 5/207* (2013.01); *G01N 2333/33* (2013.01); *G21H 5/02* (2013.01)

(58) Field of Classification Search
None
See application file for complete search history.

(56) References Cited

U.S. PATENT DOCUMENTS

| | | | |
|---|---|---|---|
| 4,830,010 A | 5/1989 | Marshall | |
| 6,264,913 B1 | 7/2001 | Wagner | |
| 6,509,002 B1* | 1/2003 | Kohno | A61K 51/1206 424/1.11 |
| 9,518,972 B2* | 12/2016 | Joseph | G01N 33/0055 |
| 2011/0143951 A1* | 6/2011 | Thompson | C12Q 1/6816 506/7 |
| 2011/0294726 A1* | 12/2011 | Pimentel | A61K 31/4164 514/2.9 |

FOREIGN PATENT DOCUMENTS

WO 2014062392 A1 4/2014

OTHER PUBLICATIONS de Preter et al. British J. Nutrition (2004) 92(3): 439-446.*
McDonald, L.C., G.E. Killgore, A. Thompson, R.C. Owens, Jr., S.V. Kazakova, S.P. Sambol, S. Johnson, and D.N. Gerding, (2005) An epidemic, toxin gene-variant strain of Clostridium difficile, N Engl J Med. 353: 2433-2441.
Zilberberg, M.D., A.F. Shorr, and M.H. Kollef, (2008) Increase in adult Clostridium difficile-related hospitalizations and case-fatality rate, United States, 2000-2005, Emerg Infect Dis. 14: 929-931.
McGlone, S.M., R.R. Bailey, S.M. Zimmer, M.J. Popovich, Y. Tian, P. Ufberg, R.R. Muder, and B.Y. Lee, The economic burden of Clostridium difficile, Clin Microbiol Infect.
Carroll, K.C., Tests for the diagnosis of Clostridium difficile infection: The next generation, Anaerobe. 17: 170-174.
Jessal, M.S., G.G. Nedeltchev, J.H. Lee, S.W. Choi, V. Atudorei, Z.D. Sharp, V. Deretic, G.S. Timmins, and W.R. Bishai, 13[C]-urea breath test as a novel point-of-care biomarker for tuberculosis treatment and diagnosis, PLoS One. 5: e12451.
Dawson, L.F., E.H. Donahue, S.T. Caftan, R.H. Barton, J. Bundy, R. McNerney, N.P. Minton, and B.W. Wren, The analysis of para-cresol production and tolerance in Clostridium difficile 027 and 012 strains, BMC Microbiol. 11: 86.
Dawson, L.F., R.A. Stabler, and B.W. Wren, (2008) Assessing the role of p-cresol tolerance in Clostridium difficile, J Med Microbiol. 57: 745-749.
Phua, T.J., T.R. Rogers, and A.P. Pallett, (1984) Prospective study of Clostridium difficile colonization and paracresol detection in the stools of babies on a special care unit, J Hyg (Lond). 93: 17-25.
Peng, A-Y.; Wang, J-P.; Cheng, J.; Zie, X-M., Zhang, Z. Tetrahedron, 2010, 66, 8238.
De Smet, R. et al. Toxicity of free p-cresol: a prospective and cross-sectional analysis Clin Chem 49, 470-8 (2003).
Asatoor et al.; "The origin of urinary tyramine. Formation in tissues and by intestinal microorganisms". Clinica Chimica Acta vol. 22, No. 2, pp. 223-229; Oct. 1, 1968.
Lord, Richard S. et al.; Clinical Applications of Urinary Organic Acids. Part 2. Dysbiosis Markers. Alternative Medicine Review vol. 13, No. 4; Jan. 1, 2008.

* cited by examiner

*Primary Examiner* — Susan M Hanley
(74) *Attorney, Agent, or Firm* — Henry D. Coleman; R. Neil Sudol

(57) ABSTRACT

The present invention is directed to methods of determining the presence or absence of a bacterial infection in a patient using isotopically-labeled tyrosine and/or isotopically-labeled p-hydroxyphenylacetic acid.

7 Claims, No Drawings

METHODS FOR DIAGNOSING BACTERIAL INFECTIONS

CROSS REFERENCE TO RELATED APPLICATIONS

This application is a U.S. national phase patent application based upon International Application No. PCT/US13/63827, filed Oct. 8, 2013, said application claims the benefit of U.S. Provisional Application No. 61/711,978, filed Oct. 10, 2012, the entirety of which applications are incorporated by reference herein.

GOVERNMENT RIGHTS

This invention was made with Government support under Grant No. DE-AC52-06NA25396 awarded by the Department of Energy, the National Nuclear Security Administration, and Los Alamos National Laboratory. The U.S. Government has certain rights in the invention.

BACKGROUND

Detecting whether a patient has a bacterial infection is important in providing suitable treatment for the patient. Often, this detection can be difficult because of the infection's location, for example, in the lungs or gastrointestinal tract. Methods of detecting the presence of particular bacteria by measuring isotopically-labeled ratios of volatile gases have been reported. See, e.g., U.S. Pat. No. 7,717,857, U.S. Published Application No. 2012/0298868, and PCT/US2013/029626. But methods of detecting other bacteria are still needed.

Epidemic infection with the intestinal pathogen *Clostridium difficile* (*C. diff*) is becoming highly important worldwide, especially in the United States with estimates that there were 300,000 cases of *C. diff.* associated disease (CDAC) in 2005 with its incidence still increasing. McDonald, L. C., G. E. Killgore, A. Thompson, R. C. Owens, Jr., S. V. Kazakova, S. P. Sambol, S. Johnson, and D. N. Gerding, (2005) An epidemic, toxin gene-variant strain of *Clostridium difficile*, N Engl J Med. 353: 2433-2441; Zilberberg, M. D., A. F. Shorr, and M. H. Kollef, (2008) Increase in adult *Clostridium difficile*-related hospitalizations and case-fatality rate, United States, 2000-2005, Emerg Infect Dis. 14: 929-931.

*C. diff.* infection results in antibiotic-associated disease, from diarrhea to the potentially fatal pseudomembranous colitis. It is believed that when the normal bowel microflora of patients is disrupted by antibiotic treatments, this allows *C. diff.* to proliferate and cause disease. *C. diff.* is also highly transmissible in hospital or long term care facilities and may cause epidemics of infection. In addition to its ability to generate host-damaging toxins, *C. diff.* also can ferment p-hydrophenylacetate, generated from tyrosine, to p-cresol. This is thought to give *C. diff.* a competitive advantage in the gut by poisoning other species. Indeed, epidemic strains of *C. diff.* are efficient producers of p-cresol.

Although methods to diagnose *C. diff.* are available, they are not suitable for estimating bacterial load in a patient to assist in a diagnosis. Moreover, the currently available methods are not able to guide treatment. For example, attempts to use cresol detection in feces as a diagnostic failed due to sensitivity issues. The current standard for diagnosis is toxigenic culture, an expensive culture-based test that takes 48 hours for results. Carroll, K. C., Tests for the diagnosis of *Clostridium difficile* infection: The next generation, Anaerobe. 17: 170-174. A number of enzyme immunoassays and PCR based techniques are being developed and tested, but it is unclear whether they can become a gold standard, or whether they are of use in monitoring treatment or cure as none of these tests are quantitative.

The average cost to treat each case of CDAC in the US is presently between $9,000 and $12,000. Furthermore, the highly transmissible nature of *C. diff.* in hospital or long-term care facilities enables it to cause epidemics of infection, and so rapid detection and effective treatment is essential in tackling *C. diff.* Accordingly, novel methods and tools for diagnosing and treating *C. diff.* are desirable.

SUMMARY

The present invention is directed to methods for determining the presence or absence of a bacterial infection in a patient comprising administering to the patient a diagnostically effective amount of an isotopically-labeled tyrosine and/or an isotopically-labeled p-hydroxyphenylacetic acid collecting one or more samples from the patient; and determining the amount of isotopically-labeled carbon dioxide and/or an isotopically-labeled para-cresol in said samples; said amount indicating the presence or absence of the bacterial infection in the patient.

DETAILED DESCRIPTION OF ILLUSTRATIVE EMBODIMENTS

The present invention is directed to methods for detecting, diagnosing, monitoring, and/or treating bacterial infections in patients. In particular, the methods of the invention can be used to detect, diagnose, monitor, and/or treat a bacterial infection wherein the bacteria has a p-hydroxyphenylacetate decarboxylase enzyme. According to the invention, an isotopically-labeled tyrosine or an isotopically-labeled p-hydroxyphenylacetic is administered to the patient. If the patient is infected with a bacteria that has a p-hydroxyphenylacetate decarboxylase enzyme, the enzyme converts the isotopically-labeled compound to a detectable compound, for example, isotopically-labeled carbon dioxide and/or isotopically-labeled p-cresol. Comparing the ratio of the isotopically-labeled carbon dioxide and/or isotopically-labeled p-cresol after administration to the ratio of the isotopically-labeled carbon dioxide and/or isotopically-labeled p-cresol prior to administration allows for the determination of whether the patient has a bacterial infection. That analysis can also provide information regarding the severity of the infection, as well as the type of bacteria present. Information regarding the severity and type of bacteria is useful in determining a course of treatment for the patient.

One bacteria known in the art that has a p-hydroxyphenylacetate decarboxylase enzyme is *C. diff.* *C. diff.*, and other bacteria, can ferment p-hydrophenylacetic acid, a tyrosine degradation product, to para-cresol using the p-hydroxyphenylacetate decarboxylase enzyme. See Scheme 1.

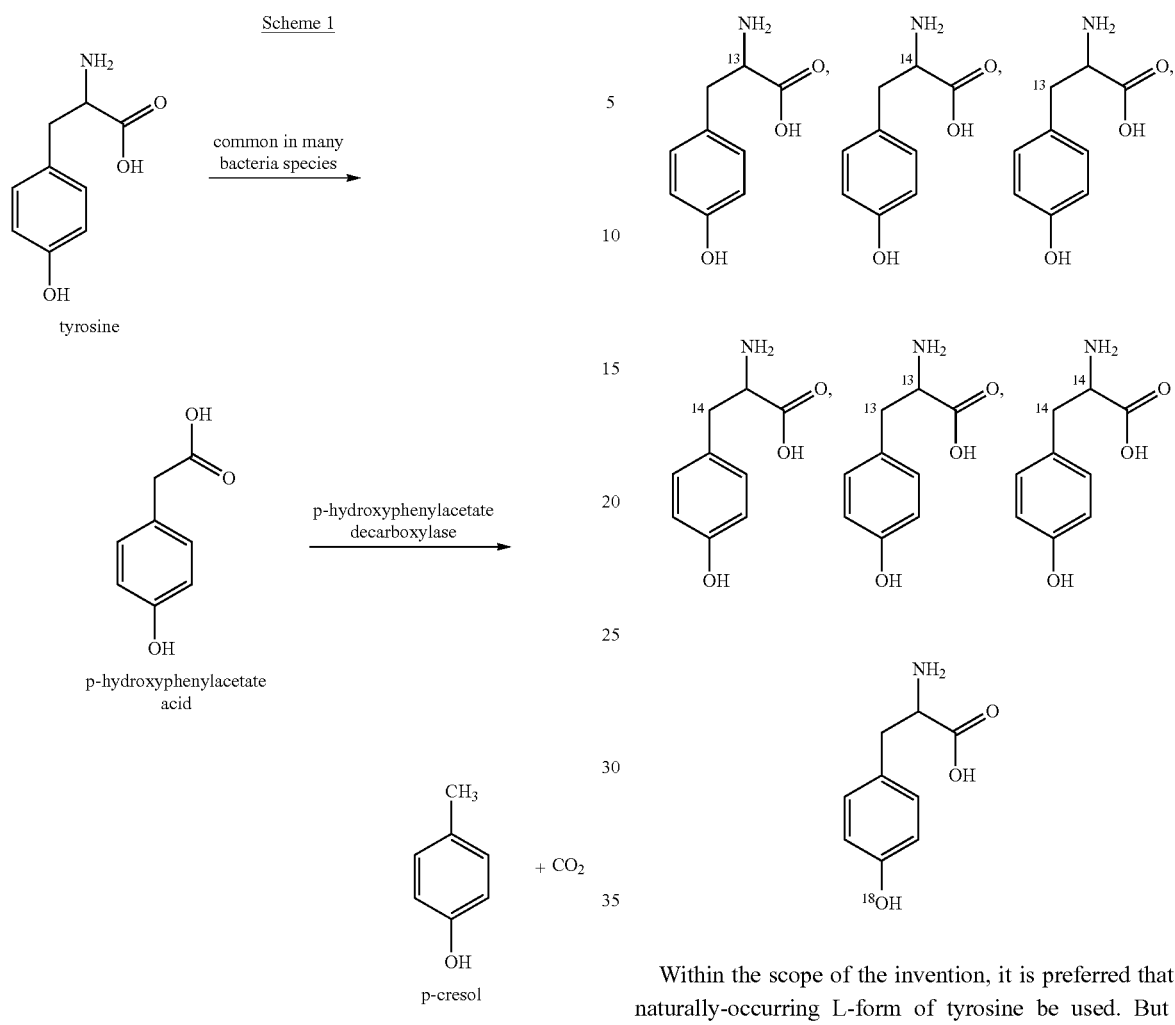

According to the invention, a patient who has a bacterial infection or who is suspected of having a bacterial infection, is administered a strategically, isotopically-labeled tyrosine or p-hydroxyphenylacetic acid. Examples of isotopic labels that can be used in the invention include one or more of $^{13}C$, $^{14}C$, and $^{18}O$. As used herein, "isotopically-labeled" refers to the presence of an isotope, for example, $^{13}C$, $^{14}C$, or $^{18}O$, in a compound that is present in an amount above natural abundance.

By administering the strategically-labeled compound, the bacterial enzyme, if present, will convert the labeled-tyrosine or labeled-p-hydroxyphenylacetic acid to a diagnostically detectable compound, for example, isotopically-labeled p-cresol or isotopically-labeled carbon dioxide. Isotopically-labeled carbon dioxide can be detected in, for example, the breath of the patient. Isotopically-labeled p-cresol can be detected in, for example, the breath, urine, and/or blood, preferably the urine and/or the blood, of the patient.

Examples of isotopically-labeled tyrosine compounds for use in the invention include:

Within the scope of the invention, it is preferred that the naturally-occurring L-form of tyrosine be used. But the D-form, as well as mixtures of D- and L-tyrosine, are also within the scope of the invention.

Examples of isotopically-labeled p-hydroxyphenyl acetic acid compounds for use in the invention include:

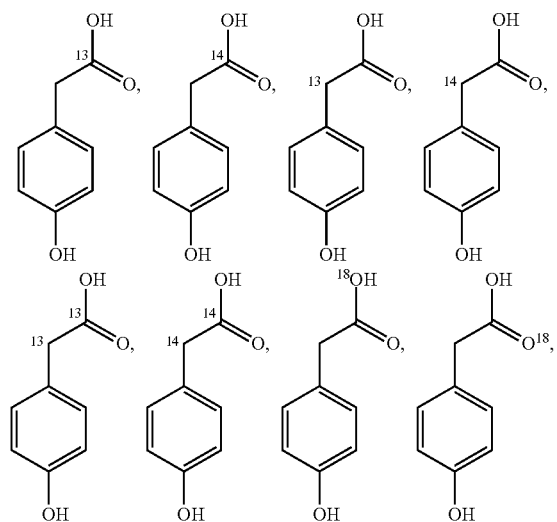

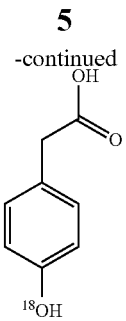

It is also envisioned that the corresponding $C_{1-6}$alkyl esters of p-hydroxyphenyl acetic acid are useful in the invention. As used herein, "$C_{1-6}$alkyl" is a branched or unbranched saturated hydrocarbon group of 1 to 6 carbon atoms. Examples include methyl, ethyl, propyl, isopropyl, butyl, isobutyl, tert-butyl, pentyl, and the like. Cyclic alkyl groups are also within the scope of the invention. Examples of $C_{1-6}$cycloalkyl groups include cyclopropyl, cyclobutyl, cyclopentyl and cyclohexyl.

The isotopically-labeled compounds for use in the invention can be purchased commercially or can be prepared according to methods known in the art. A preferred preparation for one embodiment is set forth in Scheme 2.

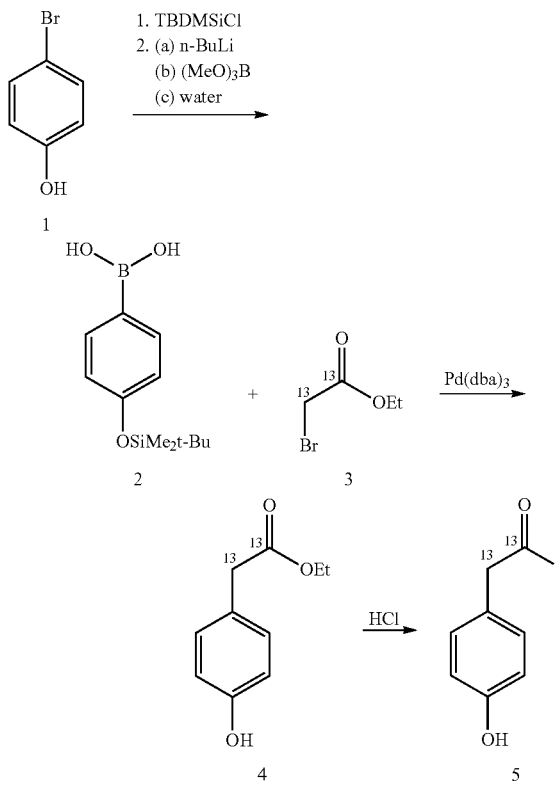

According to Scheme 2, treatment of 4-bromo-phenol (1) with a protecting group such as a silyl protecting group, e.g., t-butyl-dimethylsilyl (TBDMSi), will give rise to the protected ether compound. Transmetallation with, for example, n-butylliithium, followed by, for example, trimethyl borate, provides the resulting borate ester. The ester rapidly hydrolyzes in the presence of water to the corresponding boronic acid (2). The labeled esterified bromo acetate 3 can be made on mole scale from $^{13}CO$. Coupling of the ethyl bromo acetate with the boronic acid is effected by, for example, a palladium catalyst such as $Pd(dba)_3$. The product (4) is then subjected to, for example, acid treatment to remove the phenol protecting group and cleave the ethyl ester to give 5. An advantage of this synthesis route is that all the steps are scalable, to allow for 100 s of grams of product.

In preferred embodiments of the invention, the patient is administered an isotopically-labeled tyrosine and/or isotopically-labeled p-hydroxyphenylacetic acid that produces isotopically-labeled carbon dioxide. In these methods, the isotopically-labeled carbon dioxide is preferably detected in breath samples of the patient following administration of the isotopically-labeled tyrosine or isotopically-labeled p-hydroxyphenylacetic acid.

Examples of isotopically-labeled tyrosine that produce isotopically-labeled carbon dioxide according to the invention include:

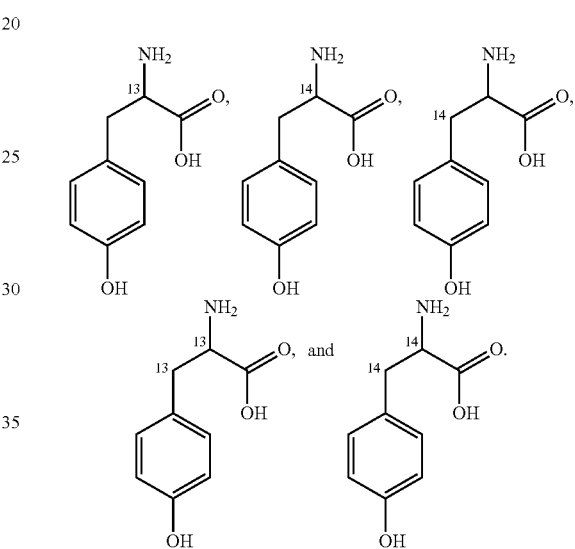

Examples of isotopically-labeled p-hydroxyphenylacetic acid that produce isotopically-labeled carbon dioxide according to the invention include:

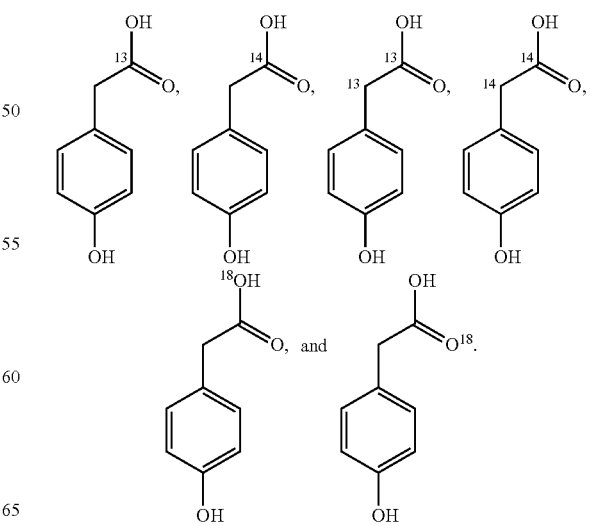

According to the invention, the patient may be administered one isotopically-labeled compound of the invention. In other embodiments, the patient may be administered a mixture of two or more isotopically-labeled compounds of the invention.

The isotopic label incorporated into the compounds of the invention will be guided by the diagnostic method to be employed. Preferably, the isotopic label is $^{13}$C. In other embodiments, the isotopic label is $^{14}$C. In yet other embodiments, the isotopic label is $^{18}$O.

The isotopically-labeled compound that produces isotopically-labeled carbon dioxide upon exposure to bacterial enzymes can be administered to the patient using any known means. In the present methods, isotopically labeled tyrosine or isotopically-labeled p-hydroxyphenylacetic acid may be administered orally or preferably, by a pulmonary (e.g. intratracheal, inhalation) route of administration. In the case of oral administration, isotopically-labeled tyrosine or isotopically-labeled p-hydroxyphenylacetic acid may be administered in standard oral dosage form, preferably as an immediate release dosage form or as an enteric dosage form, in combination with a pharmaceutically acceptable carrier, additive or excipient. Administration via injection, i.e., intramuscular, subcutaneous, peritoneal, and intradermal injection, is also within the scope of the invention.

Within the scope of the invention, one or more exhaled breath samples from the patient can be collected before the administration of the isotopically-labeled tyrosine or isotopically-labeled p-hydroxyphenylacetic acid. Such samples can be used as controls in the methods of the invention.

Following a suitable time period after administration of the isotopically-labeled tyrosine or isotopically-labeled p-hydroxyphenylacetic acid, one or more samples of exhaled breath are collected from the subject. A "suitable time period" refers to the length of time required for the isotopically-labeled compound to be converted to carbon dioxide by a bacterial enzyme. Preferably, the samples are collected after no more than 40-70 minutes following administration.

Samples can be collected in any vessel suitable for containing samples of exhaled breath, for example, a bag or vial. Samples may also be directed exhaled into a detection device by using a suitable mouthpiece. Samples can also be directly exhaled into the device by being collected using a nasal cannula from a suitable port on other respiratory equipment, for example, a ventilator.

The samples are analyzed to determine the isotopic ratio of isotopically-labeled carbon dioxide to non-isotopically-labeled carbon dioxide, i.e., $^{13}CO_2$ to $^{12}CO_2$, in the samples. Preferably, at least a majority of the exhaled breaths, and most preferably every exhaled breath, is sampled for a given time period or until the determination of the level of activity has reached a preset accuracy. The ratio of isotopically-labeled carbon dioxide to non-isotopically-labeled carbon dioxide can be measured using any of the devices known in the art.

The ratio of isotopically-labeled carbon dioxide to non-isotopically-labeled carbon dioxide may be determined and compared to a predetermined reference or control value, determined from the patient prior to the administration of the isotopically-labeled tyrosine or isotopically-labeled p-hydroxyphenylacetic acid. A measurement obtained from the patient that evidences a ratio above the reference ratio will be evidence of the existence of a bacterial infection. A measurement of approximately the reference ratio will be evidence of no infection or no bacteria that has a p-hydroxyphenylacetate decarboxylase enzyme.

A number of breaths at different times may be taken from the patient and a graph or curve generated showing the ratio of the isotopically-labeled carbon dioxide to the naturally occurring carbon dioxide in the breath of the patient as a function of time. A curve showing an increase in the ratio of the isotopically-labeled carbon dioxide to non-isotopically-labeled carbon dioxide over time, compared to a control with no infection, is evidence of the existence of a bacterial infection, for example, a *C. diff.* infection. The concentrations of isotopically-labeled carbon dioxide in the samples are compared to a standard ratio which may be obtained from a non-infected control group, or more preferably, from the patient prior to administration of isotopically-labeled tyrosine or isotopically-labeled p-hydroxyphenylacetic acid.

A curve may be fitted to the measured concentrations and then analyzed, preferably by determining the rate of rise of the curve, or by the magnitude of the plateau. Such an analysis indicates the level of activity of bacteria in the patient, which can be used to diagnose the presence of bacteria in the patient.

The measuring instrument used in the methods of the present invention can be any instrument that can measure amounts of isotopically and non-isotopically-labeled carbon dioxide. Particularly preferred instruments are mass spectrometer gas analyzers, infrared laser spectrometers, and isotope ratio mass spectrometers. These instruments are well-known in the art and are rapid, accurate, and sensitive. Examples of preferred infrared spectrometers are described in U.S. Pat. No. 5,063,275. A particularly preferred device is described in U.S. Published Application No. 2012/0298868.

The measuring instrument should be able to measure the concentration of isotopically and non-isotopically labeled carbon dioxide rapidly. Also, the measuring instrument, or an associated device, should be able to perform the associated analysis, including providing a readout, or in the case where a curve is to be generated, generating the curve and fitting the curve and providing the analysis of the curve. Such analyses will be performed rapidly. Preferably, the measuring instrument, either alone or in conjunction with the associated device, should be able to measure the concentration of isotopically and non-isotopically-labeled carbon dioxide and perform the associated analysis within about 1 minute, preferably less than 30 seconds, more preferably less than about 5 seconds.

The fitting and analysis of a curve of measured concentrations may be preferred over other approaches. The present invention, however, allows repeated breath samples to be rapidly obtained either within a single time period or multiple time periods and then maximizes both the speed and accuracy of analysis by providing a one point reference number (for the single time period analysis) above which diagnosis of active infection may be made or, in the case of multiple time periods, fitting the measured values to a curve and then calculating the rate of increase of the curve, which evidences the infection and its intensity.

An exemplary method of analysis involves the following steps. A plurality of samples of exhaled breath of the subject is collected rapidly, on the order of one sample about every few seconds or so, preferably such that at least a majority, and most preferably substantially all of the exhaled breaths of the subject at a predetermined time for a predetermined period(s) are sampled. Next, the concentration of carbon dioxide is measured and the concentration of an isotopically labeled element, such as carbon-13 (in carbon dioxide) is compared with its naturally occurring counterpart (e.g. carbon-12 in carbon dioxide) in the breath of the subject. Where the ratio of isotopically-labeled element to naturally occurring element is approximately 0 or approximately a control ratio (the control ratio is based upon measurements taken in the subject prior to administration of isotopically labeled tyrosine or isotopically-labeled p-hydroxyphenylacetic acid), then a bacterial infection as described herein is not present in the patient. In cases where the ratio of isotopically-labeled element to naturally occurring element is above a predetermined value (e.g. established from control groups) measurements above the predetermined value and/or increases of the ratio as a function of time, evidences the existence of a bacterial infection as described herein.

Although measuring and analyzing exhaled breaths from a subject for a single predetermined period represents a preferred approach to determining the existence or absence of a bacterial infection, alternative approaches also may be used. In instances where a number of measurements of exhaled breath from the subject are taken from different periods, a curve may be fitted or generated from the measured concentrations. If the ratio remains flat at the x-axis (essentially 0 or close to 0-based upon the subject or a control group) as a function of time, the presence of a bacterial infection as described herein can be ruled out. The rate of rise of the curve may be determined by calculating the integral or by derivation (calculation of the derivative), preferably after the measurement of the concentration of cleavage product(s) in each sample. The analysis of the curve indicates the level of bacterial activity in the patient. A rapid rise in the measured concentrations (a steeper curve), would evidence a high level of bacterial activity in the patient, whereas a slower rise in the measured concentrations (a shallower curve) would evidence a lower level of bacterial activity. If the infection is systemic, a greater period of time will be required for absorption and distribution of the labeled compound to the site of infection and release of labeled carbon dioxide. The technique will also prove useful in monitoring the responses of the infection to drugs. If the drugs are effective, then the bacterial load (measured as either the rate of isotopically labeled gas increase, or the value of the plateau), will continue to decrease—if the drugs are ineffective due to resistance, then this will not happen and so alternative drug therapies used.

The single point (predetermined time period) approach to diagnostic analysis has a number of advantages, for example, ease of use and rapid diagnosis. The invention also provides diagnostic methods which can be used in a clinic or a doctor's office. A single calculation may be made by taking a number of exhaled breaths from the patient or subject for the predetermined period and then analyzing for isotope-labeled gases in the sample, providing a ratio of isotopically-labeled carbon dioxide to non-isotopically-labeled carbon dioxide and comparing that ratio to a predetermined ratio obtained from the patient or from a control group.

In other approaches, the calculation of a derivative from a graph produced from a number of collection samples (from varying time periods) which provides a number of data points has advantages over other methods of analysis, such as the calculation of an integral. First, the calculation of the derivative does not require a reference breath sample to be obtained before isotopically labeled tyrosine or isotopically labeled p-hydroxyphenylacetic acid is administered to the patient. Since the derivative represents the rate of increase of the measured concentrations of carbon dioxide, the starting concentration of carbon dioxide is unimportant. However, the initial concentration of carbon dioxide in the reference breath sample is important for the proper calculation of the integral, since such an initial concentration represents a background value which must be subtracted from the measured concentrations after administration of the isotopically labeled tyrosine or isotopically labeled p-hydroxyphenylacetic acid.

After the resultant measurement has reached a predetermined level of accuracy, or after a predetermined time period has elapsed, no more samples are collected.

The present method utilizing a breath assay has a number of advantages, examples of which are recited here. First, the exhaled breath of the subject can be analyzed in real time; that is, there is relatively little delay between the time the bacterial activity takes place, and the time such activity is measured. Second, the samples of exhaled breath are obtained rapidly and are analyzed immediately in a manner which substantially increases the accuracy of the results. Depending on method, one or multiple samples may be obtained. In general, a single sample (from a number of exhaled breaths) represents a convenient method which exhibits ease of use and patient compliance. In contrast, obtaining multiple samples from the patient increases the accuracy of the test. There is also less statistical error since many samples are collected. In addition, in this aspect, since samples are preferably collected until a preset level of accuracy is reached, ambiguous results can be substantially eliminated, preventing the need for repeating the test.

The readout of isotopic ratios can be performed by, for example, sensitive gas mass spectrometry analysis and laser spectroscopy techniques, which may allow for more compact and portable devices. In certain aspects of the invention, Finnegan Delta Plus XL™ Mass Spectrometer may be used. Collection of exhaled gases may be effected using a standard gas collection bag, using a glass vial with a septum (the subject simply blows into the vial through the septum) or using any other method for collecting breaths from the subject.

In preferred embodiments of the invention, the patient is administered an isotopically-labeled tyrosine or isotopically-labeled p-hydroxyphenylacetic acid that produces isotopically labeled p-cresol. In these methods, the isotopically-labeled p-cresol is preferably detected in breath, urine, and/or blood samples of the patient following administration of the isotopically-labeled tyrosine or isotopically-labeled p-hydroxyphenylacetic acid. Preferably, the p-cresol is detected in the urine and/or blood sample(s) of the patient.

Examples of isotopically-labeled tyrosine that produce isotopically-labeled p-cresol according to the invention include:

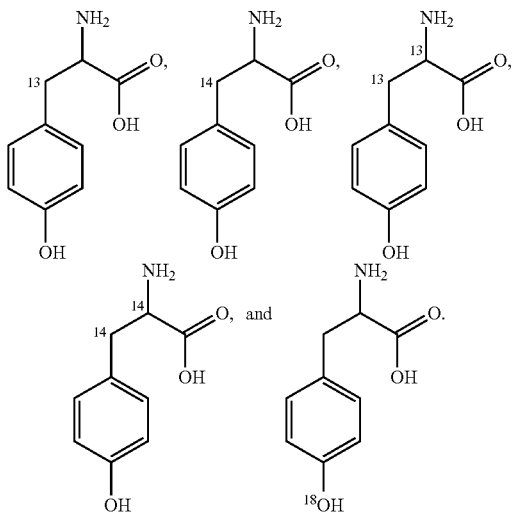

Examples of isotopically-labeled p-hydroxyphenylacetic acid that produce isotopically-labeled p-cresol according to the invention include:

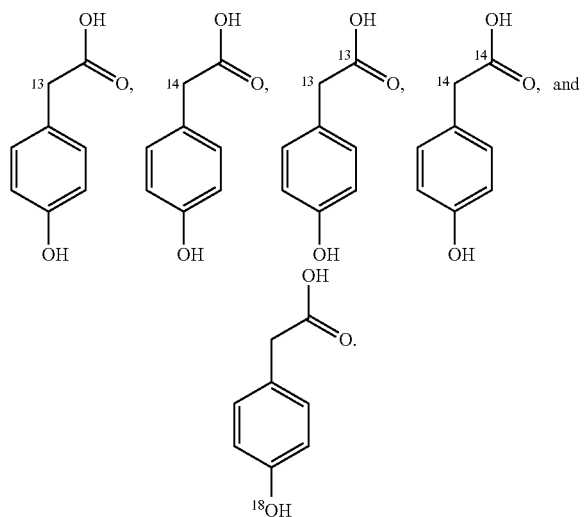

The isotopic label incorporated into the compounds of the invention will be guided by the diagnostic method to be employed. Preferably, the isotopic label is $^{13}C$. In other embodiments, the isotopic label is $^{14}C$. In yet other embodiments, the isotopic label is $^{18}O$.

Similar to the methods described above for comparing the ratio of isotopically-labeled carbon dioxide to non-isotopically-labeled carbon dioxide, one can compare the ratio of isotopically-labled p-cresol to non-isotopically-labeled p-cresol in order to determine whether the patient has a bacterial infection such as that described herein.

Oral formulations of the isotopically-labeled compounds of the invention may be formulated in enteric dosage form to promote release in the small intestine (duodenum, jejunum, ileum). Thus, the present invention also relates to pharmaceutical compositions in oral dosage forms comprising effective amounts of isotopically-labeled tyrosine and/or isotopically-labeled p-hydroxyphenylacetic acid with a pharmaceutically acceptable carrier, additive, diluent, or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, the isotopically labeled tyrosine and/or isotopically-labeled p-hydroxyphenylacetic acid is administered to the lungs of the subject via pulmonary administration, for example, intratracheal administration. The pharmaceutical compositions of the invention for pulmonary administration are usually used as inhalants. The compositions can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical compositions of the invention are used in the form of a powder, the mean particle diameter of the powder is not especially limited but, in view of the residence of the particles in the lungs, is preferably that the particles fall within the range of about 0.1 to 20 µm, and particularly about 1 to 5 µm. Although the particle size distribution of the powder pharmaceutical composition of the invention is not particularly limited, it is preferable that particles having a size of about 25 µm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the isotopically labeled compound(s) of the invention and excipients which provide for immediate release in pulmonary tissue and microparticulating the dried product. Stated more specifically, after dissolving (or dispersing) a pharmaceutically acceptable carrier, additive or excipient in an aqueous medium, isotopically-labeled compounds of the invention, in effective amounts, are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing the isotopically-labeled compound(s) of the invention and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isotopically-labeled compounds of the invention that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of isotopically-labeled compound(s) which is included in the final composition.

The pharmaceutical compositions of the invention are safe and effective for use in the diagnostic methods according to the present invention. Although the dosage of the composition of the invention may vary depending on the type of active substance administered as well as the nature (size, weight, etc.) of the patient to be diagnosed, the composition is administered in an amount effective for allowing the pharmacologically active substance to be cleaved to cleavage products to be measured. For example, the composition is preferably administered such that the active ingredient can be given to a human adult in a dose of about 0.001 to about 100 mg, about 0.01 mg to about 25 mg, about 0.05 mg to about 15 mg, about 0.1 mg to about 10 mg, about 0.5 mg to about 5 mg, about 1 to about 3 mg, and given in a single dose The form of the pharmaceutical composition of the invention such as a powder, solution, suspension etc. may be suitably selected according to the type of substance to be administered and the action of a target enzyme on tyrosine and/or p-hydroxyphenylacetic acid.

As an administration route, direct inhalation via the mouth using an inhaler is usually preferable. Since the pharmaceutical composition of the invention allows direct local administration into the airways and in particular, directly to pulmonary tissue, the active substance contained therein produces immediate effects. Furthermore, the composition is formulated as an immediate release product so that cleavage and analysis can begin soon after administration.

The compositions of the invention can also be administered intravenously. Isolated cell free extract of *C. difficile* contains 12 mU per mg of protein of the activating enzyme pHPA decarboxylase. This correlates to the production of 2.7 mL of $^{13}CO_2$ per minute in an infection in which 10 mg of bacterial protein is present when a patient is treated with a compound of the invention, for example, $^{13}C$-hydroxyphenylacetate. Oftentimes, a patient is infected with much more than 10 mg of bacterial protein with a *C. difficile* infection.

Assuming 15 liters of air is respired per minute, and with 4% exhaled $CO_2$, a patient will exhale about 600 ml of $CO_2$ per minute, of which approximately 6.6 mLs will be $^{13}CO_2$. The efficient excretion of *C. difficile*-derived 2.7 ml of $^{13}CO_2$ in this sample will significantly increase breath $^{13}CO_2$, enabling detection. Thus, efficient delivery of isotopically-labeled compound is important. Preferably, an intravenous dosage form is administered to the patient, leading to rapid increases in intestinal levels, and allowing breath testing from 10 to 120 minutes after dosage. Such dosage forms are sterile and particle-free. Preparation methods for such dosage forms are known in the art.

It will be appreciated that the diagnostic methods and compounds described herein may be suitable for use for other types of infections or diseases as well. For example, the importance of p-cresol as a uremic toxin where it derives from hydroxyphenylacetate degradation in kidney disease, indicates that $^{13}C$-labeled p-hydroxyphenylacetate may also be a viable diagnostic tool for kidney disease. De Smet, R. et al. Toxicity of free p-cresol: a prospective and cross-sectional analysis Clin Chem 49, 470-8 (2003).

It will be understood that the specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

REFERENCES

1. McDonald, L. C., G. E. Killgore, A. Thompson, R. C. Owens, Jr., S. V. Kazakova, S. P. Sambol, S. Johnson, and D. N. Gerding, (2005) An epidemic, toxin gene-variant strain of *Clostridium difficile*, N Engl J Med. 353: 2433-2441.

2. Zilberberg, M. D., A. F. Shorr, and M. H. Kollef, (2008) Increase in adult *Clostridium difficile*-related hospitalizations and case-fatality rate, United States, 2000-2005, Emerg Infect Dis. 14: 929-931.

3. McGlone, S. M., R. R. Bailey, S. M. Zimmer, M. J. Popovich, Y. Tian, P. Ufberg, R. R. Muder, and B. Y. Lee, The economic burden of *Clostridium difficile*, Clin Microbiol Infect.

4. Carroll, K. C., Tests for the diagnosis of *Clostridium difficile* infection: The next generation, Anaerobe. 17: 170-174.

5. Jassal, M. S., G. G. Nedeltchev, J. H. Lee, S. W. Choi, V. Atudorei, Z. D. Sharp, V. Deretic, G. S. Timmins, and W. R. Bishai, 13[C]-urea breath test as a novel point-of-care biomarker for tuberculosis treatment and diagnosis, PLoS One. 5: e12451.

6. Dawson, L. F., E. H. Donahue, S. T. Cartman, R. H. Barton, J. Bundy, R. McNerney, N. P. Minton, and B. W. Wren, The analysis of para-cresol production and tolerance in *Clostridium difficile* 027 and 012 strains, BMC Microbiol. 11: 86.

7. Dawson, L. F., R. A. Stabler, and B. W. Wren, (2008) Assessing the role of p-cresol tolerance in *Clostridium difficile*, J Med Microbiol. 57: 745-749.

8. Phua, T. J., T. R. Rogers, and A. P. Pallett, (1984) Prospective study of *Clostridium difficile* colonization and paracresol detection in the stools of babies on a special care unit, J Hyg (Lond). 93: 17-25.

9. Peng, A-Y.; Wang, J-P.; Cheng, J.; Zie, X-M., Zhang, Z. Tetrahedron, 2010, 66, 8238.

10. De Smet, R. et al. Toxicity of free p-cresol: a prospective and cross-sectional analysis Clin Chem 49, 470-8 (2003).

What is claimed:

1. A method for determining the presence or absence of a bacterial infection in a patient comprising:

administering to the patient a diagnostically effective amount of an isotopically-labeled compound that is

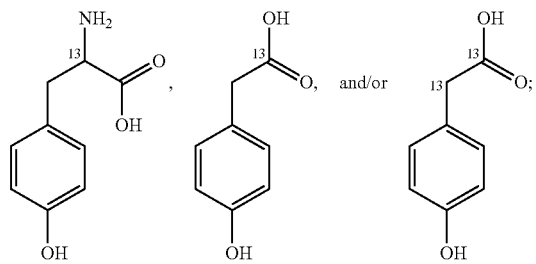

collecting one or more samples from the patient;
determining the amount of $^{13}CO_2$ in said one or more samples; and
comparing the amount of $^{13}CO_2$ in said one or more samples to an amount of $^{13}CO_2$ in one or more samples obtained from the patient prior to the administration of the isotopically-labeled compound;
said amounts indicating the presence or absence of the bacterial infection in the patient;
wherein the bacteria has the enzyme p-hydroxyphenylacetate decarboxylase.

2. The method of claim 1, wherein the bacteria of the bacterial infection is *Clostridium difficile*.

3. The method of claim 1, wherein the isotopically-labeled compound is

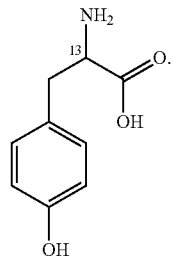 [SMILES: NC(Cc1ccc(O)cc1)C(=O)O]

4. The method of claim 1, wherein the isotopically-labeled compound is

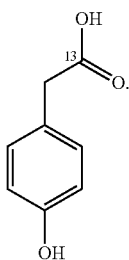 [SMILES: O=C(O)Cc1ccc(O)cc1]

5. The method of claim 1, wherein the samples are breath samples.

6. The method of claim 1, wherein the isotopically labeled compound is

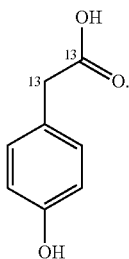 [SMILES: O=C(O)Cc1ccc(O)cc1]

7. A method for determining the presence or absence of a bacterial infection in a patient comprising:

administering to the patient a diagnostically effective amount of an isotopically-labeled compound that is

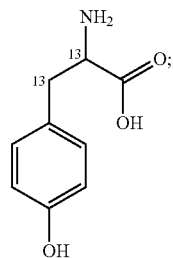 [SMILES: NC(Cc1ccc(O)cc1)C(=O)O]

collecting one or more samples from the patient;
determining the amount of $^{13}CO_2$ in said one or more samples; and
comparing the amount of $^{13}CO_2$ in said one or more samples to an amount of $^{13}CO_2$ in one or more samples obtained from the patient prior to the administration of the isotopically-labeled compound,
said amounts indicating the presence or absence of the bacterial infection in the patient;
wherein the bacteria has the enzyme p-hydroxyphenylacetate decarboxylase.

* * * * *